United States Patent [19]

Israilides et al.

[11] 4,243,686

[45] Jan. 6, 1981

[54] PROCESS FOR IMPROVING THE PALATABILITY OF STRAW FOR ANIMAL FEED

[75] Inventors: Cleanthes Israilides, Eugene; Youn W. Han; Arthur W. Anderson, both of Corvallis, all of Oreg.

[73] Assignee: The United States of America as represented by the Secretary of Agriculture, Washington, D.C.

[21] Appl. No.: 43,975

[22] Filed: May 30, 1979

[51] Int. Cl.$^3$ .............................................. A23K 1/22
[52] U.S. Cl. .................................... 426/53; 426/69; 426/626; 426/636; 426/807
[58] Field of Search .................... 426/49, 69, 53, 805, 426/807, 636, 626

[56] References Cited

U.S. PATENT DOCUMENTS

| 1,807,067 | 5/1931 | Mabee | 426/53 |
| 3,314,797 | 4/1967 | Hess et al. | 426/53 |
| 3,679,429 | 7/1972 | Mohrman et al. | 426/805 X |
| 3,930,031 | 12/1975 | Kealy | 426/805 X |
| 3,937,845 | 2/1976 | Han et al. | 426/53 |
| 4,082,677 | 4/1978 | Zollar | 426/807 X |
| 4,082,859 | 4/1978 | Katzen | 426/807 X |

OTHER PUBLICATIONS

Smith et al., "Effect of Acid Hydrolysis & Fermentation on Feeding Value of Ryegrass Straw," Proc. Western Section, Am. Soc. of Animal Science, vol. 29, Jun. (1978), pp. 240-241.

Israilides et al., "Sugar Level, Fermentability & Acceptability of Straw Treated with Different Acids," Applied & Environmental Microbiology, vol. 36, Jul. 1978, pp. 43-46.

*Primary Examiner*—R. B. Penland
*Attorney, Agent, or Firm*—M. Howard Silverstein; David G. McConnell; Theodore J. Leitereg

[57] ABSTRACT

The palatability as well as digestibility and protein content of straw is enhanced by treating it with a dilute aqueous solution of hydrochloric and phosphoric acids, ammoniating the acid-treated straw, and fermenting it with a yeast such as *Aureobasidium pullulans*. The so-treated straw is useful as a feed for ruminants and other animals.

6 Claims, No Drawings

PROCESS FOR IMPROVING THE PALATABILITY OF STRAW FOR ANIMAL FEED

DESCRIPTION OF THE INVENTION

1. Field of the Invention

The invention relates to and has among its objects the provision of novel processes for increasing the digestibility and protein content of straw whereby to provide nutritious animal feeds. Further objects of the invention will be evident from the following description wherein parts and percentages are by weight unless otherwise specified.

2. Description of the Prior Art

Over 200 million tons of cellulosic agricultural wastes are produced each year in the U.S. Naturally, the disposal of such a large quantity presents problems. Much of this waste is disposed of by burning, but such a method has been increasingly under criticism because of the air pollution that results. Many cities and states have totally or partially banned the open burning of straw and similar cellulosic agricultural wastes.

Straw contains components such as cellulose and hemicellulose which could make it desirable as an animal feed, especially for ruminants. Unfortunately, its low digestibility and low protein content presently prevent its use in feedlots.

Various methods have been advocated for enhancing the digestibility or the nutritive value of straw. For example, digestibility can be increased by treating the straw with sodium hydroxide. The nutritive value of straw can be supplemented by adding thereto a non-protein nitrogen source. In addition, efforts have been made to produce high-protein feeds by applying submerged microbial fermentation to cellulosic substrates. The above methods, however, have disadvantages either because they are too expensive or because they do not yield products of acceptable food value and digestibility, or both.

In U.S. Pat. No. 3,937,845 (hereinafter referred to as '845) there is described a process for increasing the digestibility and protein content of straw. In the patented method straw is treated with dilute sulfuric acid, ammoniated, and then fermented with a yeast such as *Candida utilis, Pullularia pullulans,* or *Trichoderma viride.*

Although the '845 process successfully enhances the digestibility and protein content of straw, its use as animal feed could be increased by improving the palatability of the treated straw. Furthermore, it has been discovered that the high sulfate content of the patented feed supplement is detrimental to the general well-being of animals that consume it.

SUMMARY OF THE INVENTION

The invention described herein provides means for obviating the problems outlined above. By application of the processes of the invention straw is converted into products which exhibit substantial increases in digestibility, palatability, and protein content. In addition, the processes of the invention are simple and do not require any elaborate equipment or expensive reagents so that economic advantages are gained.

In general, according to the invention, straw is first treated with a mixture of aqueous hydrochloric and phosphoric acids. The acid-treated straw is ammoniated and then fermented with a yeast or other microorganism.

The invention is of wide versatility and may be applied to straws of cereal grains, such as rice, wheat, oats, barley, rye, etc., and those of grasses such as orchard green, bent, red fescue, Kentucky blue, rye grass (annual or perennial), etc. The palatability, digestibility, and protein value of agricultural wastes such as leaves and stems may also be enhanced by the processes of the invention.

The primary advantage of the invention is that the palatability of the product is substantially increased over that of straw treated by known methods. Indeed, acceptability of the present product to animals is enhanced at least about two- or three-fold.

DESCRIPTION OF THE PREFERRED EMBODIMENTS

In a practice of the invention, straw—preferably in comminuted form such as chopped or ground—is first hydrolyzed by treatment with dilute aqueous mixture of hydrochloric and phosphoric acids. Generally, the normality of the hydrochloric acid and that of the phosphoric acid in the mixture is about 0.1–0.5. Hydrolysis is accomplished by mixing the straw (1 part) with about 2 to 4 parts of the aqueous acid mixture and holding the mixture at about 100° to 125° C. for about 30 to 60 minutes. It is, of course, obvious that at the higher temperatures in the said range—i.e., above 100° C.—the reaction is carried out in pressure-resistant equipment. In addition, it should be noted that the higher the temperature, the less concentrated the acid need be to attain the desired result. In a preferred embodiment of the invention, one part of straw is treated with 3 parts of a mixture containing 0.23 N hydrochloric acid and 0.15 N phosphoric acid at 121° C. for 30 minutes. The acid treatment in accordance with the invention primarily causes the hemicellulose content of the straw to be converted into monomeric sugars such as xylose, glucose, mannose, arabinose, and galactose. In a later stage of the process of the invention, these sugars are utilized as a carbon source for the growth of yeast or other microorganism.

After completion of the acid treatment, the resulting mass is adjusted to a pH of 4.0–4.5 by addition of ammonia or ammonium hydroxide. This partial neutralization step provides the appropriate pH for microbial growth in a subsequent step, and also provides a nitrogen source required for the growth of the microorganism.

Next, the ammoniated mass is inoculated with a yeast or other microorganism and fermented under aerobic conditions. Typical microorganisms useful in the process of the invention are *Phanerochete crysosporium, Candida utilis, Pullularia (Aureobasidium) pullulans,* and *Trichoderma viride.* Generally, the fermentation is conducted at a temperature of about 25°–30° C. for a period of 1 to 7 days. Preferably, some means of agitation should be applied to the fermenting mass, such as stirring, shaking, tumbling, or the like so that the mass will be properly aerated.

The inoculation may be with a pure culture of the selected microorganism or it may be with a portion of straw material which had previously been fermented in accordance with the invention. Thus in operating the process in a continuous fashion, a small portion of fermented straw may be recycled and used as the inoculum for the next succeeding fermentation.

Following completion of the fermentation, the mass is dried, for example, by conventional hot air dehydration. Products of the invention exhibit a 3- to 4-fold increase in protein content. In addition, digestibility is increased by 40% or more.

The process of the invention may be carried out batch-wise or continuously. For example, the fermentation step can be carried out in a continuous manner by providing a conveyor which carried the fermenting mass through a chamber equipped with temperature control, ventilation means, and means to tumble or otherwise agitate the mass. Other methods of continuous operation will be obvious to those skilled in the art.

An advantage of the invention is that it renders unnecessary the elaborate controls and procedures required in submerged liquid fermentations. For example, in accordance with the invention the substrate under fermentation is a moist fibrous mass containing about 20–33% solids and 80–67% water. It is pervious to air so that it can be effectively aerated by simple tumbling, shaking, or stirring. The use of spargers, pumps, and the like required in submerged liquid fermentations are not needed. Also, in accordance with the invention the various conditions of pH, temperature, and the like need not be rigorously controlled. Thus, the elaborate control mechanisms required with submerged liquid fermentations are unnecessary. Foaming problems frequently encountered in submerged liquid fermentations do not occur in the process of the invention. Another advantage of the invention is that it yields a product which in its entirety is useful as an animal feed. This is in contrast to systems of submerged liquid fermentation where the products must be harvested from the fermentation broth by centrifugation or other costly procedure.

A basic advantage of the invention is that we utilize the absorptive properties of the straw for providing a substrate in optimum condition for carrying out the fermentation. Thus, in the acid-treating step, the portion of the straw which is not hydrolyzed retains its fibrous nature and acts as a matrix to hold water, sugars, and other soluble solids. When this mass is ammoniated in the next step, the formed ammonium sulphate is held in the fibrous matrix with the other soluble components. Thus, there is made available a material in prime condition for fermentation. It contains water, mineral salts, and carbon and nitrogen sources required for growth of microorganisms. Moreover, all these components are held in the matrix of the fibrous straw material, forming a semi-solid mass so that the fermentation can be carried out in simple fashion by tumbling in the presence of air and eliminating all the elaborate equipment and controls which would be required if the substrate were a liquid.

EXAMPLES

The invention is further demonstrated by the following illustrative examples.

EXAMPLE 1

A. annual ryegrass (*Lolium multiform Lam*) was sun-dried and ground to pass a 20-mesh screen. The straw (1 part) was mixed with 3 parts of an aqueous mixture containing 0.23 N HCl and 0.15 N $H_3PO_4$ and the mixture was heated in a pressure cooker (15 psig) at 121° C. for 30 minutes.

The acid-treated straw was removed from the pressure cooker and cooled to room temperature, and enough ammonium hydroxide was mixed with it to provide a pH of 4.0–4.5.

The ammoniated material was inoculated with 5% of its weight of *Aureobasidium* (pullularia) *pullulans* (NRRL Y-6220). The inoculated sample was placed in loosely-capped bottles, which were secured to a device providing continuous tumbling action to the fermenting mass. The fermentation was carried out at room temperature for 3 days. After completion of the fermentation the products were analyzed for digestibility and acceptability to voles (*Microtus canicaudus*).

B. The above procedure was repeated except that the fermentation step was omitted.

C. The procedure in B above was followed except that 0.5 N hydrochloric acid was substituted for the mixture of acids.

D. The procedure in B above was again followed with 0.5 N phosphoric acid being substituted for the mixture of acids.

Animal feeding (Israilides et al., *Applied and Environmental Microbiology*, Vol. 35, No. 1, pages 43–46 (1978) and Smith et al., *Proceedings, Western Section, American Society of Animal Science*, Vol. 29, pages 240–241 (1978), herein incorporated by reference.

Male, uniform size, weanling, brown-tailed, meadow voles were used as test animals. Each vole was kept separately in a screenbottom cage and fed from an aluminum cup (10×5 centimeters). Feed and water were provided ad libitum. The diet consisted of 51% ground corn, 30% straw, 12% soybean meal, 5% corn oil, and 2% mineral mix (*Journal of Nutrition*, Vol. 24, pages 799–802 (1976)). Tests were conducted for 10 days using 20 voles per test.

The results are summarized below.

| Run | Treatment | Consumption by voles (g) |
|---|---|---|
| A | HCl/$H_3PO_4$, *A. pullulans* | 2.93 |
| B | HCl/$H_3PO_4$ | .84 |
| C | HCl | .28 |
| D | $H_3PO_4$ | .35 |

EXAMPLE 2

The undigested residue of rumen fermented straw (RR straw) has a hemicellulose content of about 23% while the whole straw has a hemicellulose content of about 24.5%. RR straw has a very low digestibility (about 5%) as compared to whole straw (42–48%). This is probably due to bound complex of hemicellulose with lignin which renders it unavailable to rumen microorganisms.

RR straw was prepared as follows: About 200 g of ryegrass straw was fermented with 8 l of rumen fluid under a carbon dioxide atmosphere at 39° C. for 7 days. The undigested residue was filtered and washed through four layers of cheesecloth and dried at room temperature.

RR straw was hydrolyzed as described in Run A above with HCl/$H_3PO_4$ and fermented with *A. pullulans* (Run E) and *Phanerochete crysosporium* (Run F).

In vitro rumen digestibility (IVRD) was determined as follows: A 0.5 g sample of the RR straw and 35 ml of rumen fluid were placed in a 50 ml screw-capped bottle. The rumen fluid was obtained from a fistulated Holstein bull and was mixed with a mineral and buffer solution at a ratio of 1:1. The mineral and buffer solution contained 9.88 g NaHO₃, 9.3 g Na₂HPO₄.12 H₂O, 0.47 g NaCl, 0.57 g KCl, 0.04 g CaCl₂ and 0.06 g MgCl₂ in 1 liter of water. The rumen fluid was gassed with $CO_2$ and warmed to 39° C. prior to inoculation with the candidate material. The mixture of the candidate material and rumen fluid was incubated for 3 days at 39° C. and then filtered through a sintered glass crucible (Pyrex, 20 ml, coarse) and the solid material on the filter dried overnight at 105° C. The weight loss was reported as percentage of digestibility. The results obtained are summarized below.

| Run | Treatment | IVRD (%) |
|---|---|---|
| E | HCl/H₃PO₄, P. crysosporium | 31.9 |
| F | HCl/H₃PO₄, A. pullulans | 23.4 |
| Control | None | 6.2 |

EXAMPLE 3

Two feeding trials were carried out as follows:

In trial 1 voles were fed diets (Example 1) containing straw that was treated as in Run A of Example 1 (Run G) and Run B of Example 1 (Run H). As a control corn meal was fed to the voles.

In trial 2 the voles were fed diets (Example 1 ) containing straw that was prepared according to the procedure described in the Examples section of U.S. Pat. No. 3,937,845, by treatment with sulfuric acid, ammoniation and fermentation (Run J). Corn meal was employed in the control feeding.

The results are tabularized below. Feed efficiency is defined as units of feed needed to gain a unit of body weight; a lower value for feed efficiency is preferred.

| Trial | Run | Treatment | Daily feed intake (g) | Average daily weight gain (g) | Feed efficiency (g feed per g weight gain) |
|---|---|---|---|---|---|
| 1 | G | HCl/H₃PO₄, A. pullulans | 6.1 | 0.52 | 11.7 |
|  | H | HCl/H₃PO₄ | 6.1 | 0.50 | 12.2 |
|  | Control | None | 5.4 | 0.68 | 8.0 |
| 2 | J* | H₂SO₄, C. utilis | 4.9 | 0.29 | 17.0 |
|  | Control | None | 4.6 | 0.69 | 6.6 |

*The voles fed this diet containing straw treated with sulfuric acid and fermented with *C. utilis* gained little weight and showed poor health exhibiting rough hair, unkempt appearance, and lethargic behavior.

Having thus described our invention, we claim:

1. A process for increasing the palatability, digestibility, and protein content of straw, which comprises
   (a) mixing the straw with an aqueous solution containing 0.1-0.5 normal hydrochloric acid and 0.1-0.5 normal phosphoric acid in the proportion of one part of straw to about 2-4 parts of aqueous solution at a temperature of about 100°-125° C. for a period of about 30-60 minutes.
   (b) adding to the acid treated straw an amount of ammonia to provide a pH of about 4.0-4.5,
   (c) aerobically fermenting the ammoniated acid-treated straw with a microorganism at a temperature of about 25°-30° C. for a period of about 1-7 days, and
   (d) drying the fermented product.

2. The process of claim 1 wherein the microorganism is selected from the group consisting of *Pullalaria (Aureobasidium) pullulans, Phanerochete crysosporium, Candida utilis,* and *Trichoderma viridi.*

3. The process of claim 1 wherein the microorganism is *Pullaria (Aureobasidium) pullulans.*

4. The process of claim 1 wherein the microorganism is *Phanerochete crysosporium.*

5. The process of claim 1 wherein the microorganism is *Candida utilis.*

6. The process of claim 1 wherein the microorganism is *Trichoderma viridi.*

* * * * *

UNITED STATES PATENT AND TRADEMARK OFFICE
CERTIFICATE OF CORRECTION

PATENT NO. : 4,243,686
DATED : January 6, 1981
INVENTOR(S) : Cleanthes Israilides et al.

It is certified that error appears in the above—identified patent and that said Letters Patent is hereby corrected as shown below:

Column 5, line 1, "$NaHO_3$" should read -- $NaHCO_3$ --.

Signed and Sealed this

Twelfth Day of May 1981

[SEAL]

Attest:

RENE D. TEGTMEYER

Attesting Officer     Acting Commissioner of Patents and Trademarks